United States Patent
Moore

(10) Patent No.: US 6,570,170 B2
(45) Date of Patent: May 27, 2003

(54) TOTAL RELEASE METHOD FOR SAMPLE EXTRACTION FROM A CHARGED-PARTICLE INSTRUMENT

(75) Inventor: Thomas M. Moore, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 0 days.

(21) Appl. No.: 10/085,968

(22) Filed: Feb. 28, 2002

(65) Prior Publication Data

US 2002/0121614 A1 Sep. 5, 2002

Related U.S. Application Data

(60) Provisional application No. 60/272,820, filed on Mar. 1, 2001.

(51) Int. Cl.$^7$ .......................... H01J 37/08; A61N 5/00; G21G 5/00; G21K 5/10
(52) U.S. Cl. .............................. 250/492.21; 250/492.1; 250/492.2; 250/309
(58) Field of Search ............................... 250/309, 288, 250/400, 491.1, 492.1, 492.2, 492.21, 492.22, 492.23

(56) References Cited

U.S. PATENT DOCUMENTS

| | | | | |
|---|---|---|---|---|
| 4,939,364 A | | 7/1990 | Ishitani et al. ............... | 250/309 |
| 5,093,572 A | | 3/1992 | Hosono ....................... | 250/310 |
| 5,171,717 A | | 12/1992 | Broom et al. ................ | 437/226 |
| 5,270,552 A | | 12/1993 | Ohnishi et al. .............. | 250/307 |
| 5,866,021 A | * | 2/1999 | Yagi et al. ..................... | 216/84 |
| 6,420,722 B2 | * | 7/2002 | Moore et al. ........... | 250/559.27 |
| 2001/0045511 A1 | * | 11/2001 | Moore et al. ................ | 250/221 |
| 2002/0079463 A1 | * | 6/2002 | Shichi et al. ............ | 250/492.1 |

FOREIGN PATENT DOCUMENTS

| | | | | | |
|---|---|---|---|---|---|
| JP | 04076437 A | * | 3/1992 | ............ | G01N/1/28 |
| JP | 05052721 A | * | 3/1993 | ............ | G01N/1/28 |
| JP | 05302876 A | * | 11/1993 | ............ | G01N/1/32 |
| JP | 08003768 A | * | 1/1996 | ............. | C23F/4/00 |
| JP | 08209340 A | * | 8/1996 | ........... | C23C/14/32 |

OTHER PUBLICATIONS

Ishitani, T., et al., "Simple Calculation on Topography of Focused–Ion–Beam Sputtered Surface", Japanese J. of Applied Physics Part 2–Letters, vol. 28, No. 2, Feb. 1989, pp. L320–L32. Japan.

Ishitani, T., et al., "Proposal for Device Transplantation using a Focused Ion Beam", Japanese J. of Applied Physics Part 2–Letters, vol. 29, No. 1, Jan. 1990, pp. L188–L190. Japan.

Ishitani, T., et al., "Micromachining and Device Transplantation Using Focused Ion Beam", Japanese J. of applied Physics Part 1–Regular Papers Short Notes & Review Papers, vol. 29, No. 10, Oct. '990, pp. 2283–2287. Japan.

(List continued on next page.)

Primary Examiner—John R. Lee
Assistant Examiner—Bernard E. Souw
(74) Attorney, Agent, or Firm—John A. Thomas

(57) ABSTRACT

A sample (180) is separated from an integrated circuit chip or a semiconductor wafer (100) for examination so that the resulting sample (180) can be moved to a location for examination by TEM, SEM or other means. A sample (180) portion of the chip or wafer (100) containing an area of interest is separated with a two cuts (140, 160) at two different angles (130, 170) by a focused ion-beam (120). Only after the sample (180) is separated is it fixed to a micromanipulator probe (190). The sample (180) is then moved by the probe (190) to the location for examination.

17 Claims, 13 Drawing Sheets

OTHER PUBLICATIONS

Herlinger, L. R., et al., "TEM Sample Preparation Using A Focused Ion Beam and A Probe Manipulator", Proceedings of the 22nd International Symposium for Testing and Failure Analysis, Nov. 18–22, 1996, Los Angeles, California.

Morris, S., et al., "A Technique for Preparing TEM Cross Sections to a Specific Area Using the FIB," ISTFA '91: The 17th International Symposium for Testing & Failure Analysis, Los Angeles, California, USA/Nov. 11–15, 1991.

Szot, J., et al., "Focused ion beam micromachining for transmission electron microscopy specimen preparation of semiconductor laser diodes," J. Vac. Sci. Technol. B 10(2), Mar./Apr. 1992.

Ishitani, T., et al., "Focused–ion–beam "cutter" and "attacher" for micromachining and device tramsplantation," J. Vac. Sci. Technol. B 9(5) Sep./Oct. 1991.

Yamaguchi, A., et al., "Transmission electron microscopy specimen preparation technique using focused ion beam fabrication: Application to GaAs metal–semiconductor field effect transistors," J. Vac. Sci. Technol. B 11(6), Nov./Dec. 1993.

Nikawa, K., "Applications of focused ion beam technique to failure analysis of very large scale integrations: A review," J. Vac. Sci. Technol. B 9(5), Sep./Oct.

Overwijk, M., et al., "Novel scheme for the preparation of transmission electron microscopy specimens with a focused ion beam," J. Vac. Sci. Technol. B 11(6), Nov./Dec. 1993.

Young, R.J., et al., "High–Yield and High–Throughput TEM Sample Preparation Using Focused Ion Beam Automation", Proceedings of the 24th International Symposium for Testing and Failure Analysis, Nov. 15–19, 1998, Dallas, Texas.

* cited by examiner

TOTAL RELEASE METHOD FOR SAMPLE EXTRACTION FROM A CHARGED-PARTICLE INSTRUMENT

CLAIM FOR PRIORITY

This application claims the priority of the U.S. Provisional Application filed Mar. 1, 2001, under serial No. 60/272,820 and bearing the same title.

COPENDING U.S. APPLICATION

Applicant is one of the inventors in copending U.S. application, Ser. No. 09/863,571, now U.S. Pat. No. 6,420, 782 D2 for "Method for Sample Separation and Lift-Out," filed May 23, 2001.

BACKGROUND

The present invention relates to a method for separating a sample, and a method for preparing the separated sample for analysis, in cases where analysis is desired; and particularly relates to a method for separating a minute sample region from a substrate such as a semiconductor wafer.

This application describes embodiments in which a sample is cut out of a semiconductor wafer or other object by use of a focused ion beam (FIB) for further processing, modification, or analysis, and analyzed, if desired, through the use of a transmission electron microscope (TEM), scanning electron microscope (SEM), or by other means.

Certain inspection methods of samples from integrated circuit wafers and other materials require the fabrication of an electron-transparent (<50 nm thickness) region on the sample that contains the place of interest for observation. The traditional means for preparing a sample for TEM inspection involves isolating the region of interest by means of a diamond wafering saw, precision wafer cleaving apparatus, or mechanical grinding. With this method, it is difficult to set the place of observation and direction of the sample desirably and precisely. It is necessary to carry out a step in which a region having a length of several mm, a width of 100–500 $\mu$m, and the thickness of the semiconductor wafer, and including a portion to be analyzed, is mechanically separated from the chip of an integrated circuit or semiconductor wafer. In the case of a semiconductor wafer, this requires dividing the wafer and precludes the further use of this wafer for production. Additional steps involving mechanical grinding, polishing and low energy ion milling (<3 keV Argon), are required to thin the excised portion in certain areas to the thickness required for TEM inspection. This procedure is acceptable for the inspection of repetitive structures, but is challenging and time consuming for site-specific inspections in which a specific micron-sized target region must be exposed for TEM inspection.

The use of the FIB offers advantages over conventional mechanical TEM sample preparation due to its ability to inspect the integrated circuit wafer and use the ion beam to thin the sample to the thickness required for TEM inspection. In an established method for TEM sample preparation in a FIB instrument, a chip, or "ribbon," having a length of several mm, a width of 100 $\mu$m to several mm, and the thickness of the semiconductor wafer, and containing the region of interest for observation, is cut out from a semiconductor integrated circuit wafer by use of a diamond wafering saw, precision wafer cleaving apparatus, or mechanical grinding, or in some combination of these techniques. In the case of a semiconductor wafer, this requires dividing the wafer and precludes the further use of this wafer for production. The ribbon is then mounted on a modified TEM grid. The portion of the ribbon containing the region of interest is formed into an electron-transparent sample by focused ion beam milling in the FIB. The thin film region of the sample can then be inspected in the TEM by irradiation with an electron beam.

A method for performing the entire TEM sample preparation within the FIB known as "in-situ lift-out" relies on a mechanical probe within the sample vacuum chamber of the charged-particle instrument to extract the excised sample containing the region of interest once it has been released from the wafer by ion milling in the FIB. In-situ lift-out typically uses the gas-assisted material deposition capability of the FIB to connect the excised sample containing the region of interest to the tip of the mechanical probe. The excised sample containing the region of interest can then be attached to a modified TEM grid by means of the gas-assisted material deposition capability of the FIB, and separated from the mechanical probe by ion milling in the FIB. The region of interest can then be thinned to an electron-transparent thickness using ion milling in the FIB. In a previously practiced method for in-situ lift-out (U.S. Pat. No. 5,270,552 to Ohnishi, et al.), the tip of the mechanical probe is connected to the smaller sample before the sample is completely released from the wafer. This practice has disadvantages overcome in the present invention.

Due to re-deposition of material during charged-particle milling, it is often difficult to determine if the cuts being made into the material are complete. There is a danger the operator using the conventional method will damage the sample by prematurely attempting lift-out. There is also a possibility that more time than necessary will be spent on the charged-particle milling to ensure that material re-deposited during the milling process has been completely removed.

Further, if the mechanical probe is connected by material deposition to the sample containing the region of interest, and the charged-particle milling is performed from two different angles relative to the surface of the wafer, re-deposition during the second milling operation into the cut from the first milling operation may require tilting the sample back to the charged-particle incident angle used for the first milling operation to re-open the initial cuts. This would require disconnecting the mechanical probe to re-do the first milling operation, re-orienting the sample to the final milling angle, and then re-connecting the mechanical probe to the smaller sample for lift-out, possibly damaging the sample. Even more important is the considerable increase in time to complete the inspection operation if the probe must be disconnected and re-connected.

Even though the mechanical performance of the in-situ mechanical probe can be optimized for typical operating conditions of the charged-particle instrument, unexpected transient mechanical events may produce a force that will result in relative displacement between the probe and sample, or a stress on the connection between the probe and sample or on the sample itself. Such stress can break the attachment between the probe and sample, and possibly damage the sample. Again, re-connection of the probe causes unacceptable delay in the inspection operation.

There is a need for an in-situ lift out method that avoids the dangers of premature lift-out; that allows re-orientation of the sample for additional milling without modifying the sample; and, that minimizes the time during which a transient mechanical event can place damaging stress on the probe and sample or cause unacceptable delays. The present invention solves all of these problems inherent in the prior art.

SUMMARY

The invention is preferably embodied in a method for sample separation and lift-out comprising the following steps:

First, a wafer, usually but not necessarily a semiconductor device, is positioned inside a FIB instrument. The wafer will have an area of interest, or target. The ion beam is positioned at substantially normal incidence to the plane of the wafer. In an alternative embodiment, the first position of the ion beam will be at some acute angle to the plane of the wafer.

The ion beam is used to cut a substantially U-shaped first cut into the wafer; the U-shaped first cut at least partially surrounds the target. Next, the wafer is re-positioned with respect to the ion beam. Then the ion beam is preferably positioned at an angle in the range of 45 to 60 degrees to the plane of the wafer.

A second cut is made in the wafer with the ion beam, undercutting the target, so that a sample is completely released from the wafer. Next, a probe is fixed to the released sample, preferably with ion-beam deposition, and the sample and the wafer can then be separated.

The order of the cuts may be reversed. In this case, the ion beam is positioned at an angle less than 90 degrees to the plane of the wafer. Then the ion beam is used to make a first cut in the wafer, undercutting the target. Next, the wafer is repositioned with respect to the ion beam by turning the wafer approximately 180 degrees, and the ion beam is re-positioned to substantially normal incidence to the plane of the wafer. The ion beam then cuts a U-shaped second cut into the wafer; the U-shaped second cut at least partially surrounding the target and intersecting the first cut, so that the sample is completely released from the wafer. A probe is attached to the sample as before.

DRAWINGS

DISCLOSURE

The method described in this disclosure (the "total release" method) comprises connection of the tip of a probe (190) to a sample (180) only after the sample (180) is completely and totally released from a larger sample, or wafer (100), by milling with a charged-particle beam, or "FIB." This is a significant improvement over the prior-art methods. In this application, we describe the object under examination as a "wafer." Usually, the sample (180) includes some area of interest for inspection, called the "target" here.

The "wafer" (100) need not be a semiconductor device. It may, for example be a micromechanical device, or any solid substance whatever requiring TEM, SEM, or other analysis, such as particles, granules, biological materials, or thin films. The FIB instrument may be either a single-beam model, or a dual-beam model. Typical FIB instruments are those manufactured by FEI Company of Hillsboro, Oreg., as models 200, 820, 830, or 835.

The total release method allows for instant and definite indication that the sample release procedure has been completed successfully, thus saving time. If pressure is applied by the probe (190) to the sample (180) during the final milling procedure, mechanical displacement of the tip of the probe (190), or a change in mechanical stress in the probe (190) device, can be used to indicate that the sample release procedure has been successfully completed. If the probe (190) does not apply pressure to the sample (180) during the final milling procedure, but is rather positioned over the sample (180) to prevent the sample (180) from leaving the pit from which it was released due to (for example) static electric interactions, movement of the sample (180) within the pit can be used as an indicator that the sample release procedure has been successfully completed.

The mechanical probe (190) is typically a component of a micro-manipulator tool that is attached to the FIB instrument with vacuum feed-through. A typical such micro-manipulator tool is the Model 100, manufactured by Omniprobe, Inc. of Dallas, Tex.

First Milling Operation

Figure 1:
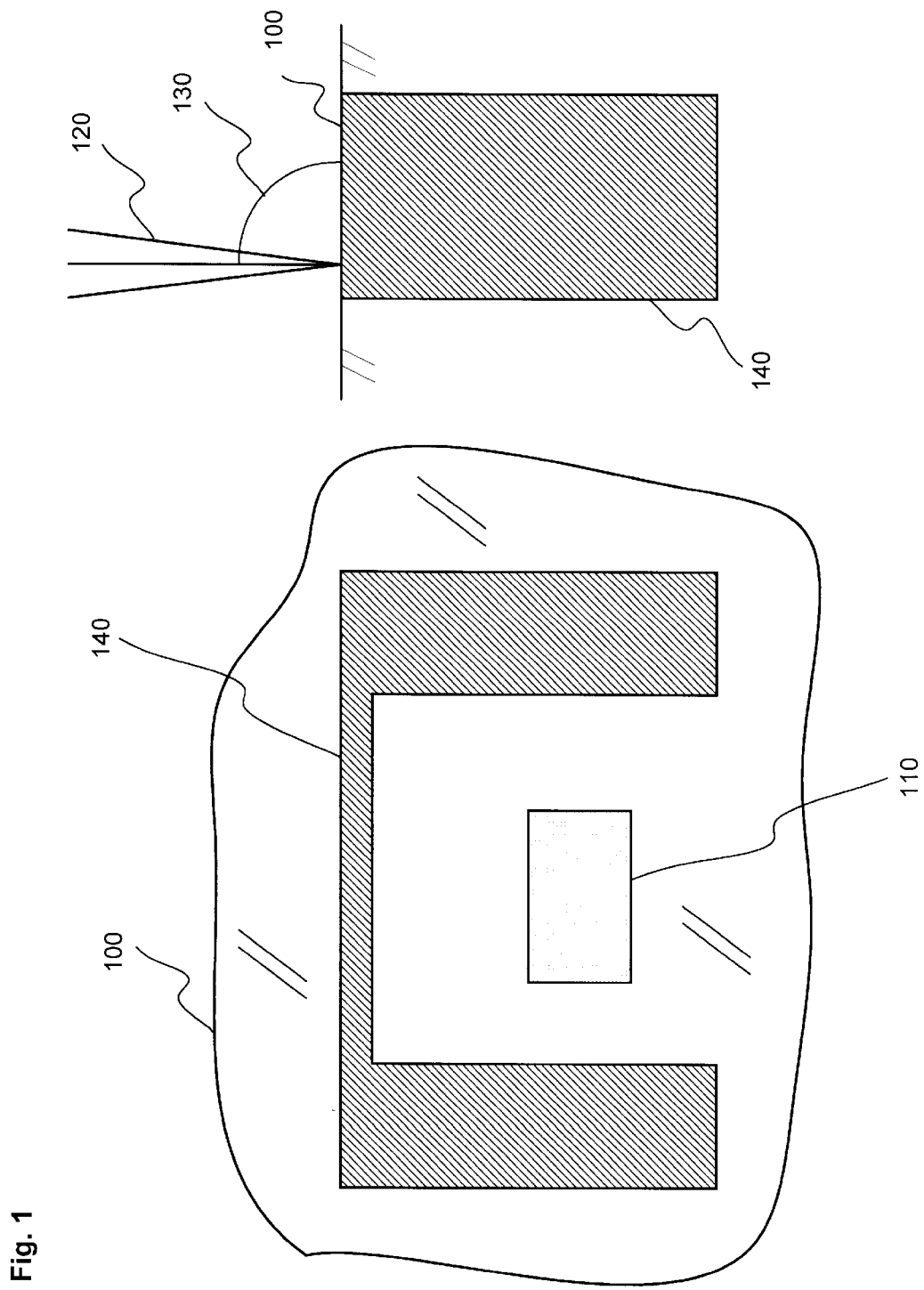
FIG. 1 shows a top view and side view of a typical pattern for the first ion milling operation.

FIG. 1 shows a typical pattern for the first ion milling operation. In this example, the first milling operation is performed with the FIB (120) at a first angle (130) of normal incidence to the sample surface. A U-shaped pattern is milled to at least partially surround the target (110), thus defining a sample (180) containing a target (110). This first cut (140) completes the first milling operation. Alternatively, the path of the can be a rectangular path enclosing the target completely. Both techniques are equivalent.

Second Milling Operation

Figure 2:
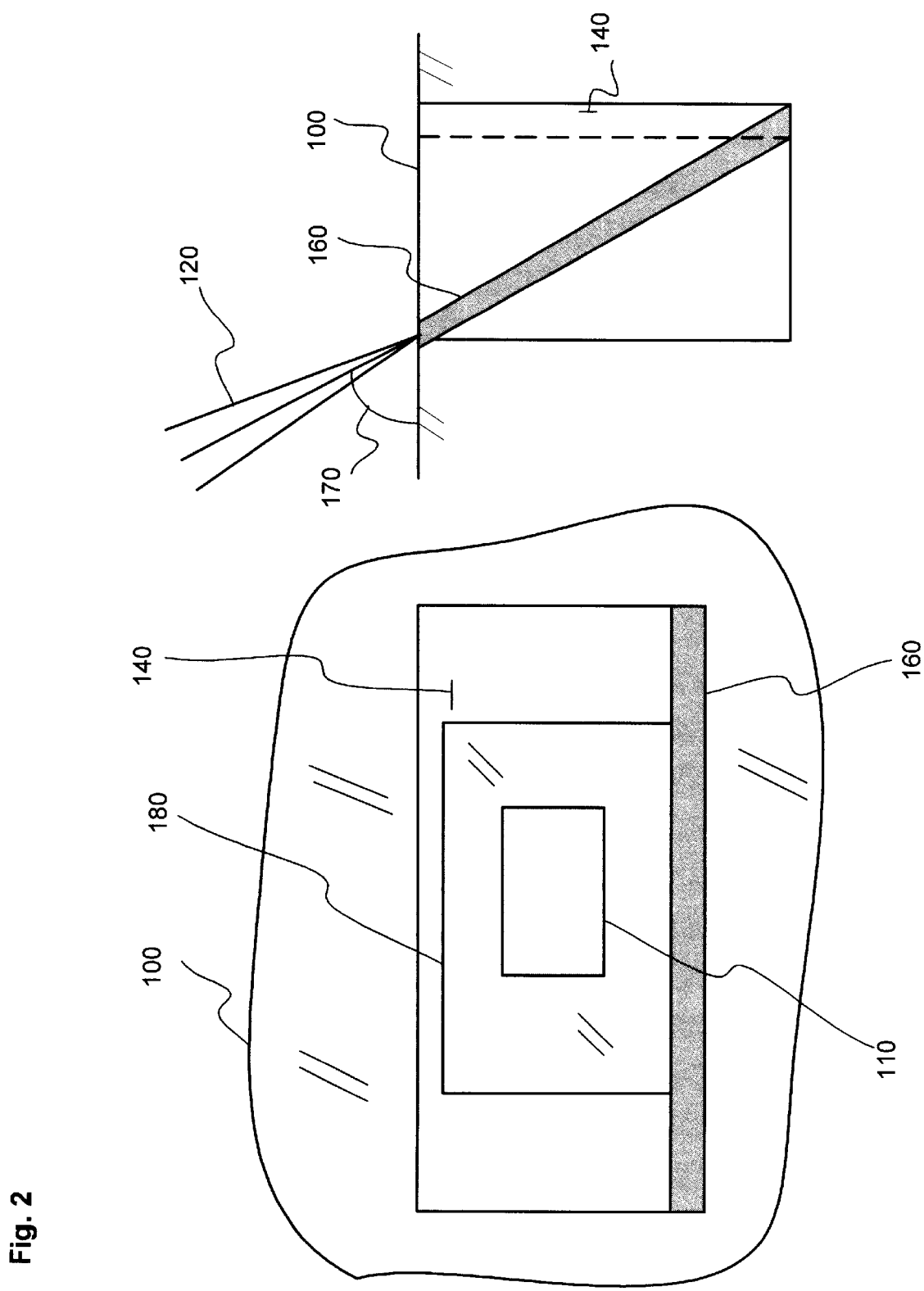
FIG. 2 shows a top view and side view of the second and final milling operation.
Figure 3:
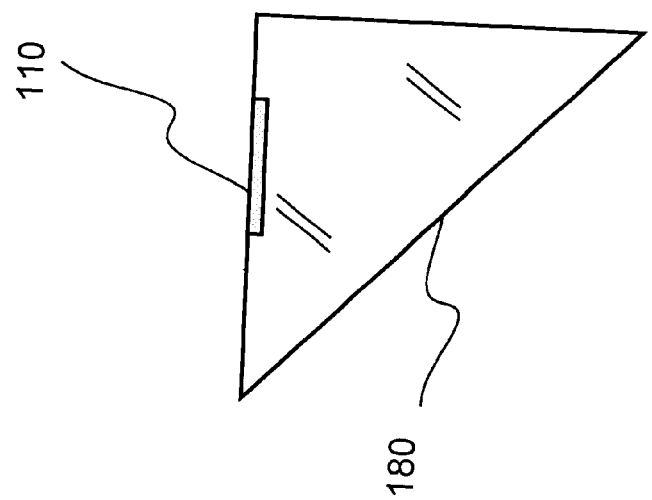
FIG. 3 shows a top view and side view of the preferred shape of the sample to be separated from the wafer.
Figure 3:
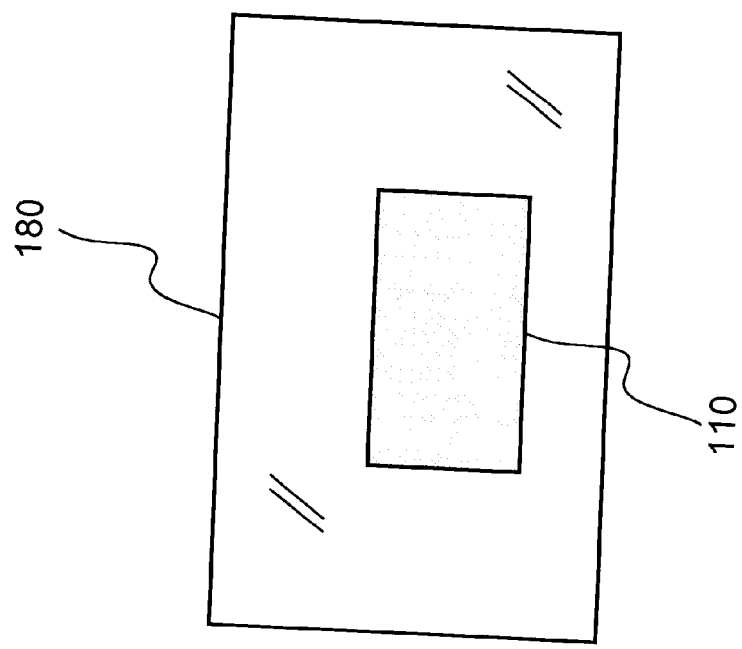
Figure 4:
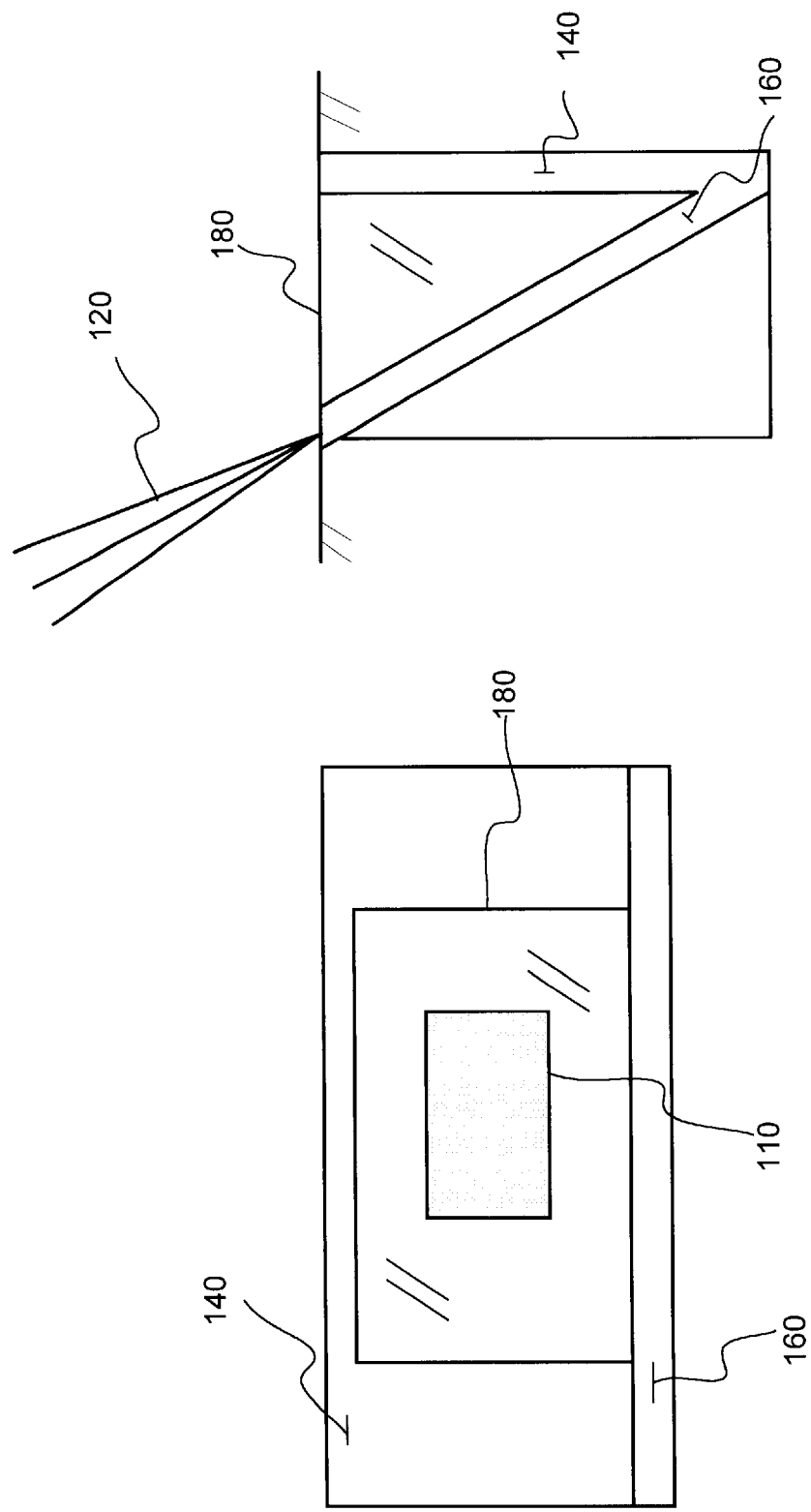
FIG. 4 shows a top view and side view of the sample being separated from the wafer.

The second and final milling operation, shown in FIG. 2, is performed at a second angle (170) to undercut and release the sample (180), after the wafer has been turned approximately 180 degrees and thus repositioned with respect to the ion beam. The second angle (170) of milling, for example, can be any angle less than ninety degrees to the plane of the wafer (100), although an angle of 45–60 degrees relative to normal incidence is preferable. The area of the second cut (160) by the FIB (120) is shown in FIG. 2 and the following figures. In this example, the desired shape of the sample (180) is described in FIGS. 3 and 4. The probe (190) can be used to provide pressure to the sample (180) during the final milling operation, or can be used to contain the sample (180) within the pit in the wafer (100) during final milling.

Figure 5:
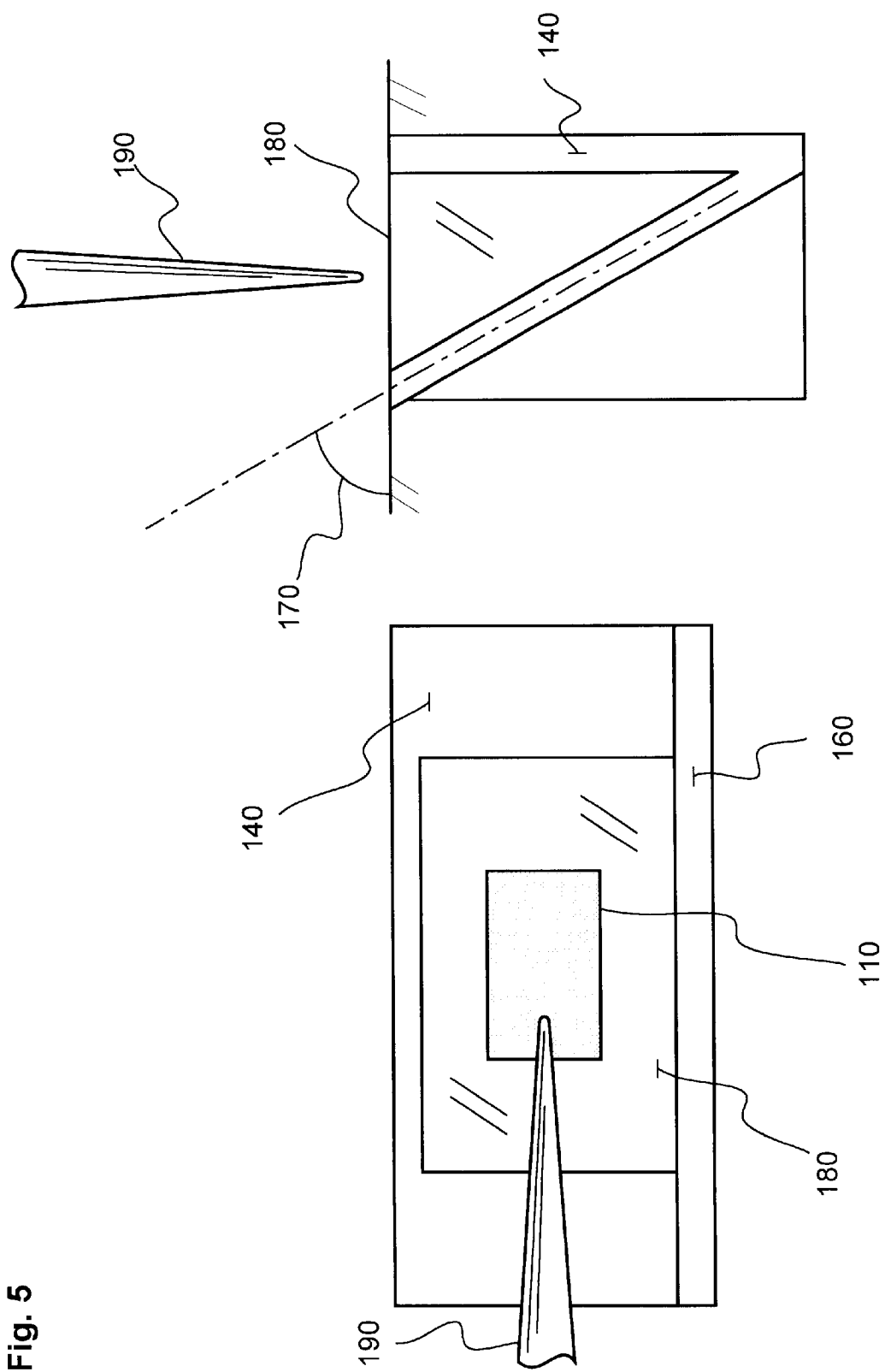
FIG. 5 shows a top view and side view of the probe over the sample after its release from the wafer.
Figure 6:
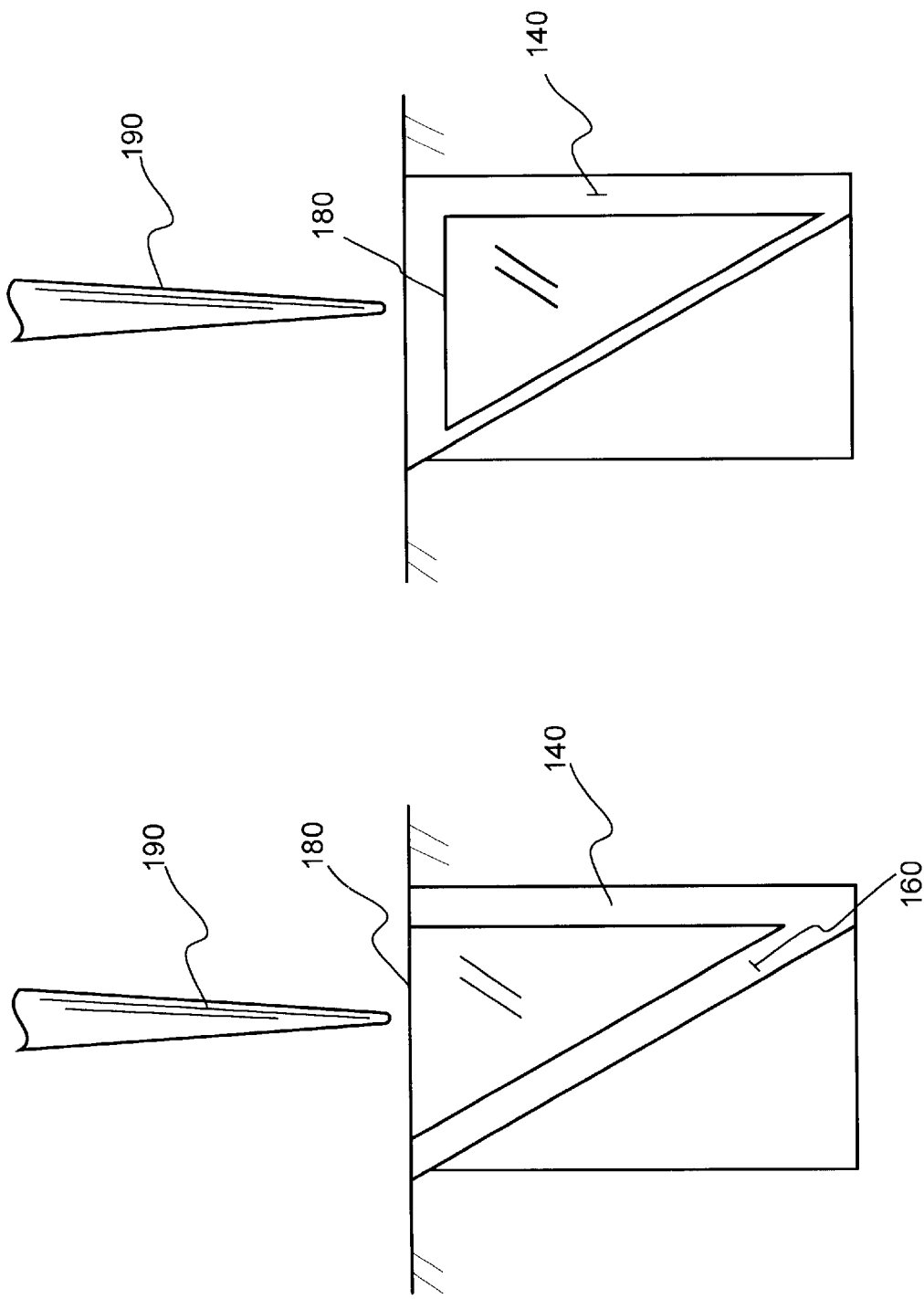
FIG. 6 shows a top view and side view of the wafer and sample, after release, illustrating how movement of the sample can be used to detect completion of the sample release procedure.

FIG. 5 shows the position of the probe (190) over the sample (180) to prevent loss of the sample due to local static electric charges. The probe (190) may be placed, unconnected, over the sample after the first cut (140). FIG. 6 shows how mechanical movement of the sample (180) after total release can be used to indicate completion of the sample release procedure.

Figure 7:
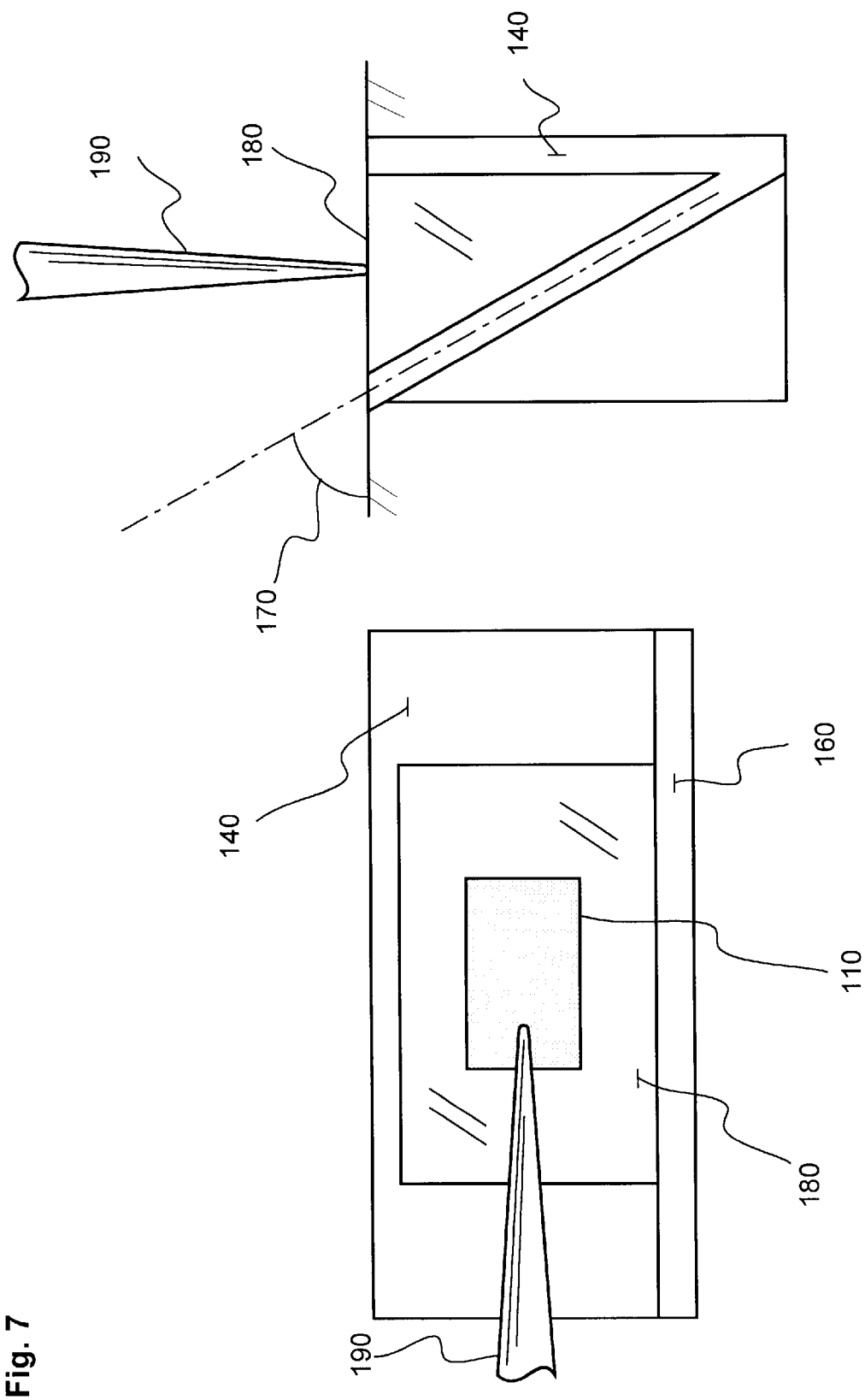
FIGS. 7 and 8 show top views and side views of the wafer and the sample, after release, where pressure is applied to the sample by a probe to detect completion of the sample release procedure.
Figure 8:
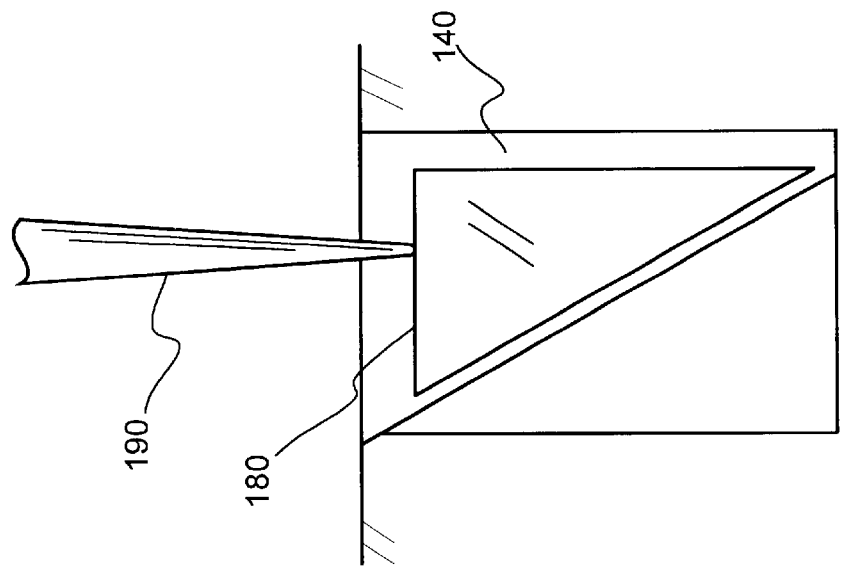
Figure 8:
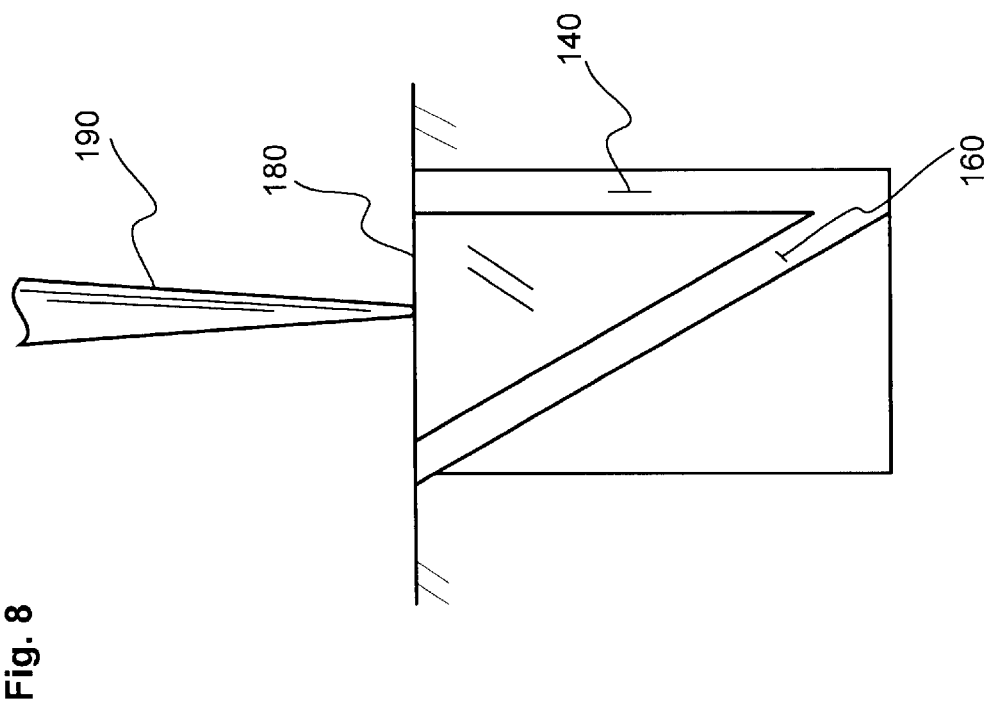

As shown in FIGS. 7 and 8, if pressure is applied by the probe (190), or multiple probes (190), to the sample (180) during the final milling procedure, mechanical displacement of the probe (190), or a change in mechanical stress in the probe (190) device, can be used as an indication that the sample release procedure has been successfully completed. For example, a downward vertical displacement of 1 $\mu$m of the body of the probe (190) after contact will produce sufficient stress in the tip of the probe (190) to move the sample (180) into the pit in the wafer (100) after total release. The moment of total release can be determined by inspection of the position of the sample (180), or by sensing the change of stress in the probe (190).

In-Situ Lift-Out

Figure 9:
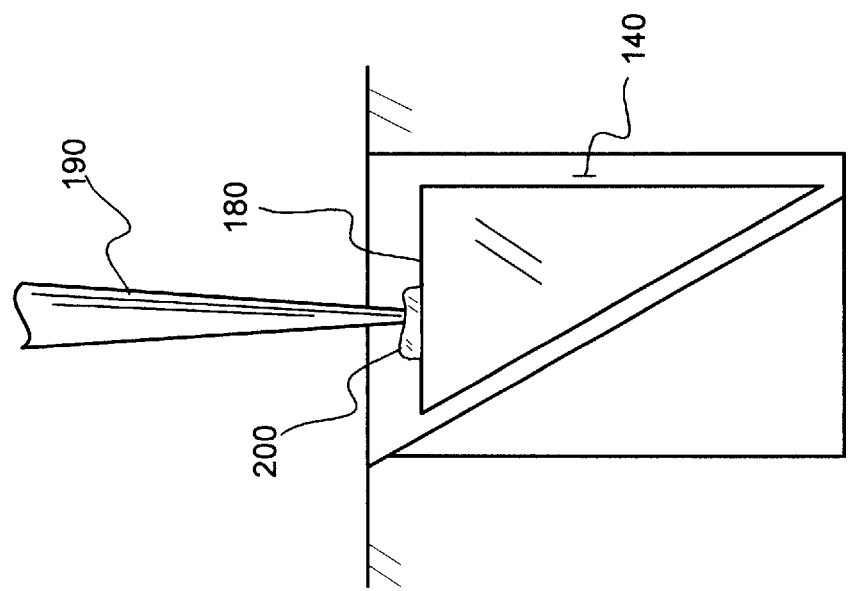
FIG. 9 shows a top view and a side view of the wafer and sample, after release, where lift-out is accomplished by connecting the probe to the sample.
Figure 9:
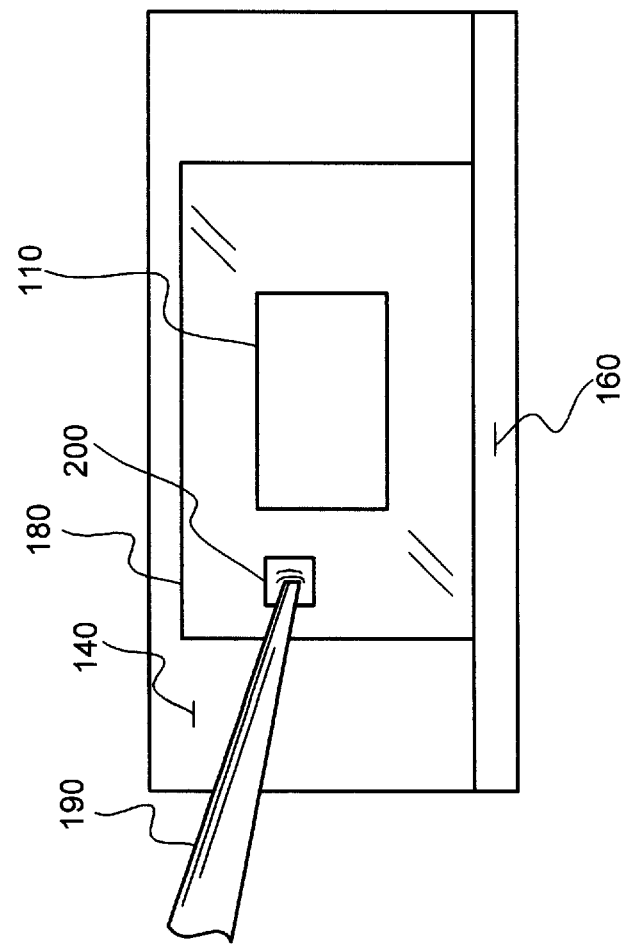
Figure 10:
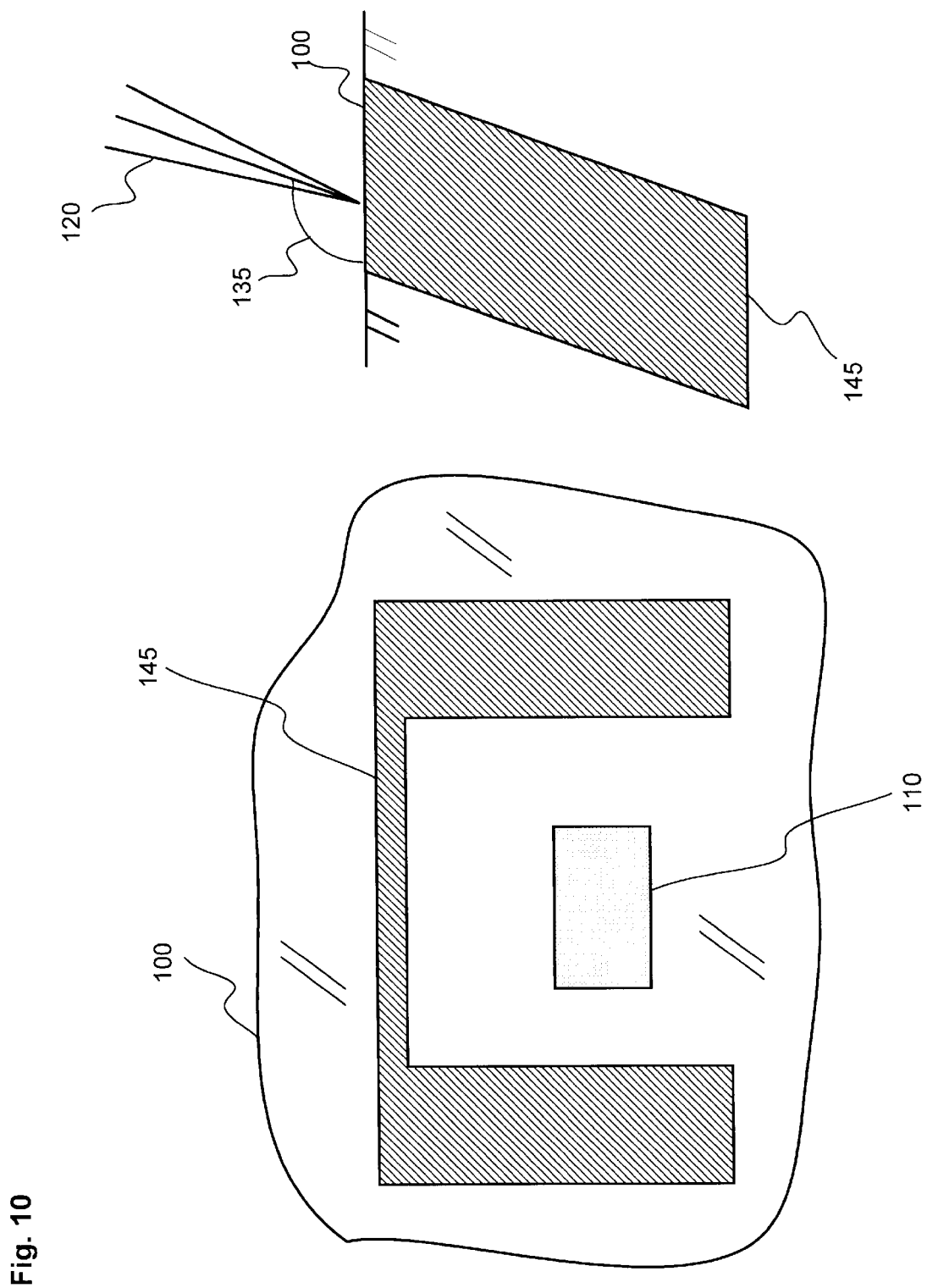
FIG. 10 shows a top and side view of a pattern for the first ion milling operation in an alternative embodiment of the invention.

FIGS. 9 and 10 show the procedure for connecting the probe (190) to the sample (180) after total release by use of material deposition in the charged-particle instrument. The operator then preferably uses charged-particle beam induced deposition, such as ion beam induced material deposition in the FIB instrument, to form a weld (200) that fixes the tip of the probe (190) to the sample (180). Other methods may be used to fix the probe (190) to the sample, such as electron-beam induced deposition or electrostatic attraction, or adhesives. The lift-out translation can be accomplished by raising the probe (190) or by lowering the wafer (100). Once removed from the wafer (100), the sample (180) can be removed from the charged-particle device, retained within the charged-particle device for further processing or inspection of the target (110), or translated to another sample holder within the charged-particle instrument and transferred to it using material deposition and material milling procedures.

First Alternative Embodiment

The above is one embodiment of the total release method. For example, due to differences in the orientation of the charged-particle beam or beams in commercially available charged-particle instruments, it may be more convenient to perform the milling operations in the opposite order described here. In this case, the milling operation performed at the second angle (170) to normal incidence would be performed first, and the normal incidence milling operation second, and the probe (190) would approach the sample in a direction so as not to interfere with the final milling operation.

Second Alternative Embodiment

An alternative embodiment of the invention is depicted in FIGS. 10 through 13. In this embodiment, the first milling cut with the FIB (120) is made at some angle less than 90 degrees to the plane of the wafer, for the first angle (135). This first angle (135) is preferably in the range of 45 to 60 degrees. A side view of a typical alternative first cut (145) is depicted in FIG. 10. A U-shaped pattern is milled to at least partially surround the target (110), thus defining an alternative sample (185) containing a target (110). This first cut (145) completes the first milling operation. Alternatively, the path of the can be a rectangular path enclosing the target completely.

Figure 11:
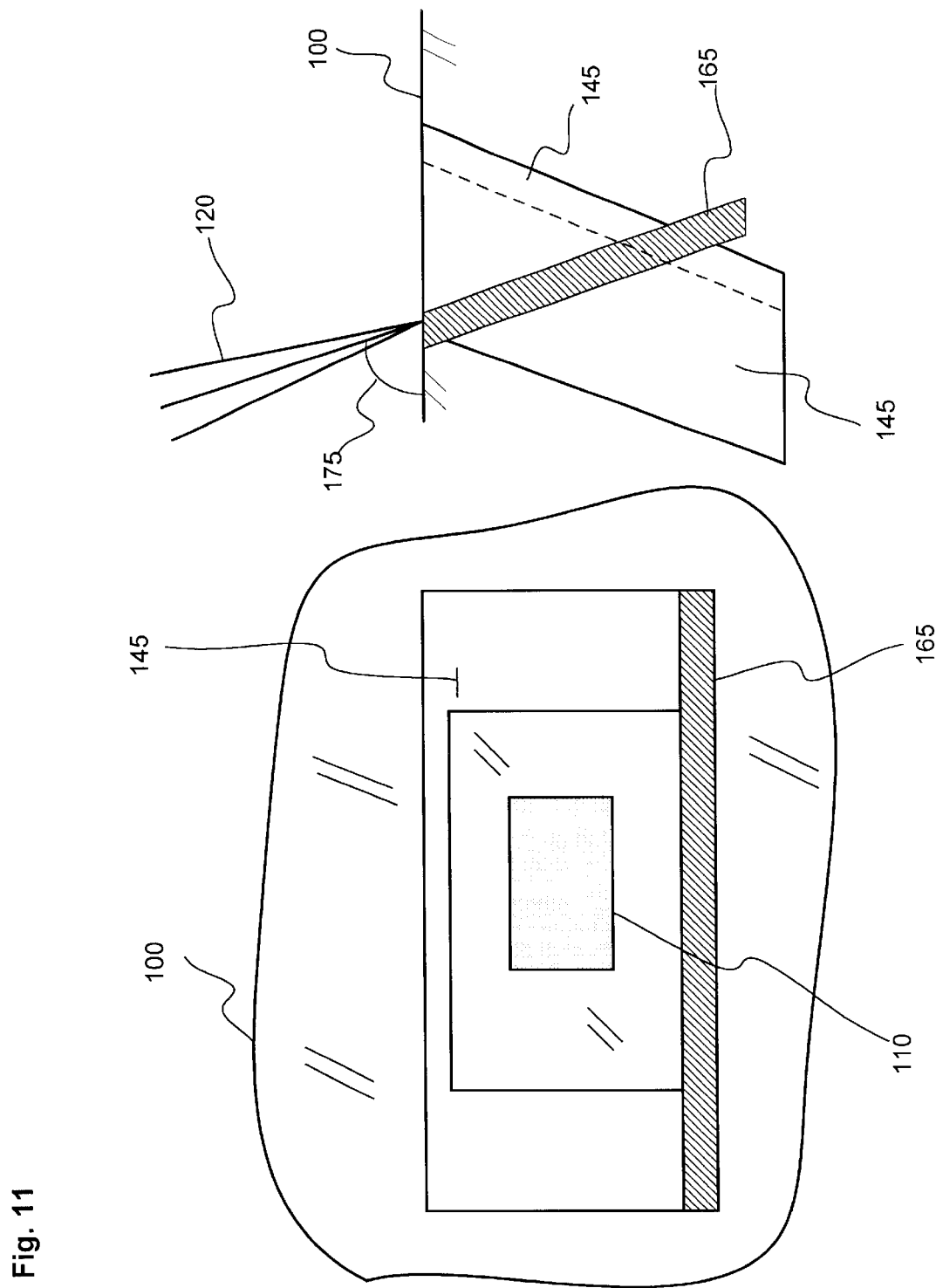
FIG. 11 shows a top and side view of the second and final ion milling operation in an alternative embodiment of the invention.
Figure 12:
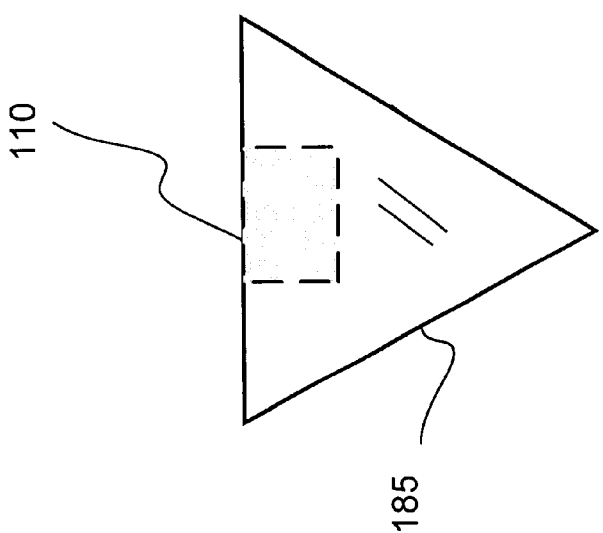
FIG. 12 shows a top and side view of the released sample in the alternative embodiment of the invention.
Figure 12:
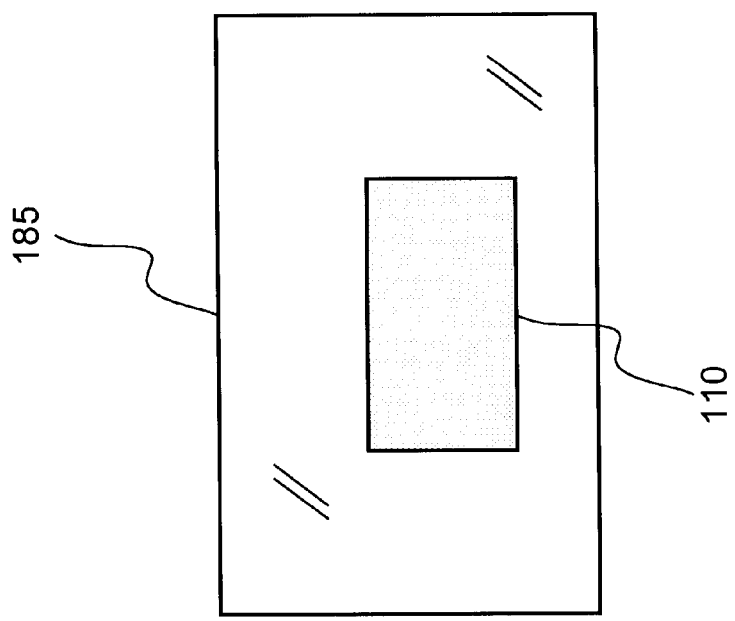
Figure 13:
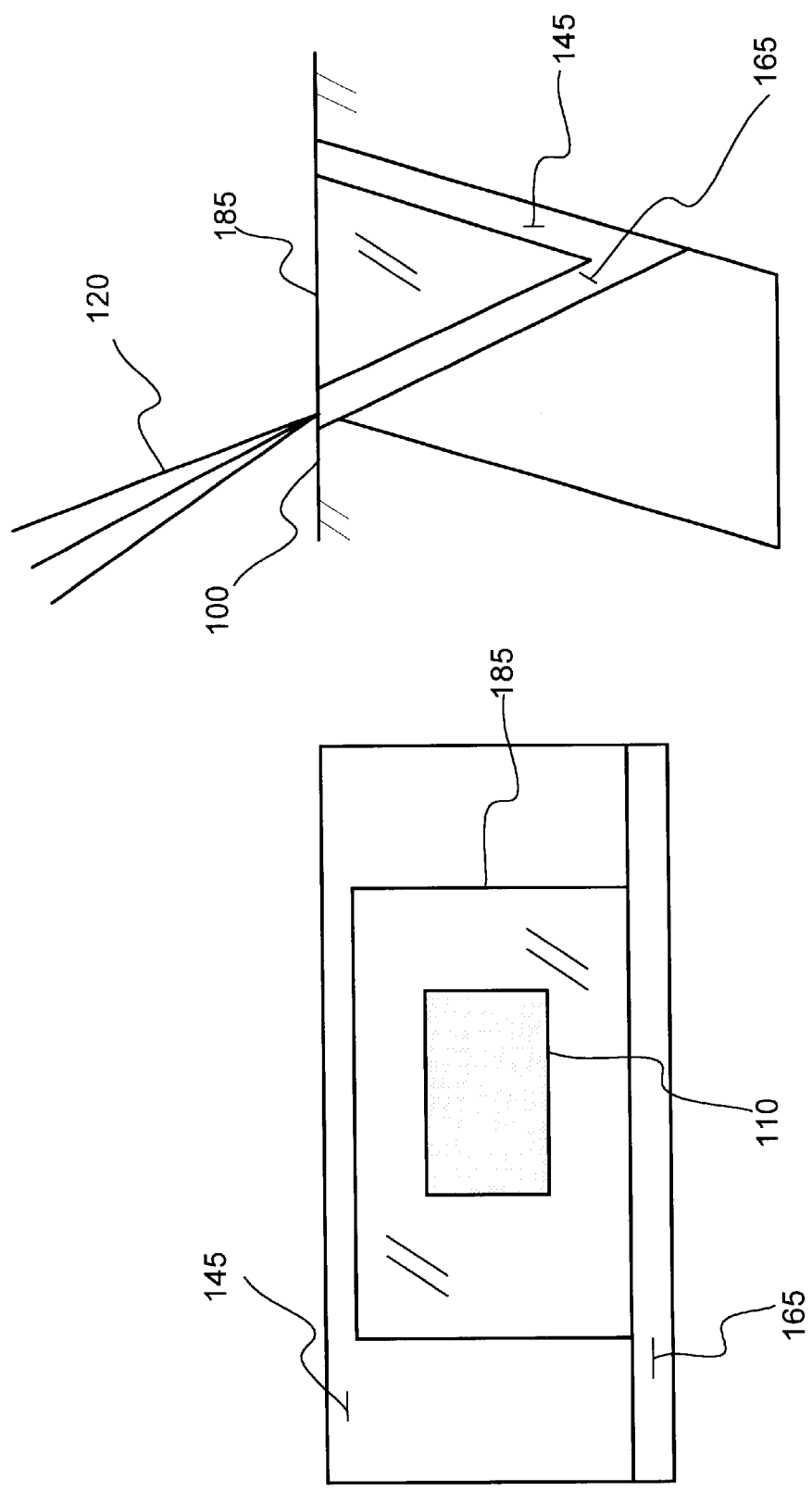
FIG. 13 shows a top and side view of the probe over the sample after its release from the wafer in the alternative embodiment of the invention.

The second milling operation in the alternative embodiment, shown in FIG. 11, is performed at a second angle (175) to undercut and release the sample (185), which now has roughly the cross-section of an isosceles triangle. The second angle can be any angle less than 90 degrees, although again, an angle of 45 to 60 degrees relative to normal incidence is preferable. FIGS. 12 and 13 show the desired shape of the sample (185) in this alternative embodiment.

After the release of the sample (185) by this alternative method, it may be manipulated and lifted out as previously described for the preferred embodiment.

Since those skilled in the art can modify the specific embodiments described above, I intend that the claims be interpreted to cover such modifications and equivalents.

I claim:

1. A method for sample separation and lift-out comprising the steps of:
   a. positioning a wafer, the wafer having a target, inside a FIB instrument;
   b. positioning an ion beam at substantially normal incidence to the plane of the wafer;
   c. cutting with the ion beam a first cut into the wafer; the first cut at least partially surrounding the target;
   d. re-positioning the wafer with respect to the ion beam;
   e. positioning the ion beam at an angle less than 90 degrees to the plane of the wafer;
   f. cutting with the ion beam a second cut in the wafer, undercutting the target, so that a sample containing the target is completely released from the wafer after the second cut; and thereafter
   g. fixing the tip of a probe to the released sample; and,
   h. separating the sample and the wafer.

2. The method for sample separation and lift-out of claim 1, where the probe is fixed to the wafer with ion-beam deposition.

3. The method for sample separation and lift-out of claim 1, where the probe is fixed to the sample with electron-beam deposition.

4. The method for sample separation and lift-out of claim 1, where the probe is fixed to the sample by electrostatic attraction.

5. The method for sample separation and lift-out of claim 1, where the probe is fixed to the sample with adhesive.

6. The method for sample separation and lift-out of claim 1, where the angle of the ion beam less than 90 degrees is in the range of 45 to 60 degrees.

7. The method for sample separation and lift-out of claim 1, where the first cut of the ion beam follows a rectangular path on the surface of the wafer; the path at least partially surrounding the target.

8. The method for sample separation and lift-out of claim 1, where the first cut of the ion beam follows a U-shaped path on the surface of the wafer; the path at least partially surrounding the target.

9. The method for sample separation and lift-out of claim 1 where the release of the sample from the wafer is assisted by first lowering the wafer.

10. The method for sample separation and lift-out of claim 1, where the wafer is a semiconductor device.

11. The method for sample separation and lift-out of claim 1, where the wafer is a micromechanical device.

12. The method for sample separation and lift-out of claim 1 where the effects of the ion beam are assisted by gas-assisted etching.

13. A method for sample separation and lift-out comprising the steps of:
   a. positioning a wafer, the wafer having a target, inside a FIB;
   b. positioning an ion beam at an angle less than 90 degrees to the plane of the wafer;
   c. cutting with the ion beam a first cut in the wafer, undercutting the target;
   d. re-positioning the ion beam to substantially normal incidence to the plane of the wafer;
   e. cutting with the ion beam a second cut into the wafer; the second cut at least partially surrounding the target and intersecting the first cut, so that a sample containing the target is completely released from the wafer after the second cut; and thereafter
   f. fixing the tip of a probe to the released sample; and,
   g. separating the sample and the wafer.

14. A method for sample separation and lift-out comprising the steps of:
   a. positioning a wafer, the wafer having a target, inside a FIB instrument;
   b. positioning an ion beam at an angle less than 90 degrees to the plane of the wafer;
   c. cutting with the ion beam a first cut into the wafer; the first cut at least partially surrounding the target;
   d. re-positioning the wafer with respect to the ion beam;
   e. positioning the ion beam at an angle less than 90 degrees to the plane of the wafer;
   f. cutting with the ion beam a second cut in the wafer, undercutting the target, so that a sample containing the target is completely released from the wafer after the second cut; and thereafter
   g. fixing the tip of a probe to the released sample; and,
   h. separating the sample and the wafer.

15. The method of claim 14 where the angle of the ion beam less than 90 degrees is in the range of 45 to 60 degrees.

16. The method of claim 14 where the first cut of the ion beam follows a U-shaped path on the surface of the wafer; the path at lease partially surrounding the target.

17. A method for sample separation and lift-out comprising the steps of:
   a. positioning a semiconductor device, the semiconductor device having a target, inside a FIB;
   b. positioning an ion beam at substantially normal incidence to the plane of the semiconductor device;
   c. cutting with the ion beam a substantially U-shaped first cut into the semiconductor device; the U-shaped first cut at least partially surrounding the target;
   d. re-positioning the semiconductor device with respect to the ion beam;
   e. positioning the ion beam at an angle in the range of 45 to 60 degrees to the plane of the semiconductor device;
   f. cutting with the ion beam a second cut in the semiconductor device, undercutting the target, so that a sample containing the target is completely released from the semiconductor device after the second cut; and thereafter
   g. fixing the probe to the released sample with ion-beam deposition; and,
   h. separating the sample and the semiconductor device.

* * * * *

UNITED STATES PATENT AND TRADEMARK OFFICE
CERTIFICATE OF CORRECTION

PATENT NO. : 6,570,170 B2 Page 1 of 1
DATED : May 27, 2003
INVENTOR(S) : Thomas M. Moore It is certified that error appears in the above-identified patent and that said Letters Patent is hereby corrected as shown below:

<u>Column 8,</u>
Line 11, the word "lease" should be -- least --.

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,570,170 B2  Page 1 of 1
APPLICATION NO. : 10/085968
DATED : May 27, 2003
INVENTOR(S) : Thomas M. Moore It is certified that error appears in the above-identified patent and that said Letters Patent is hereby corrected as shown below:

In claim 2, replace "fixed to the wafer" with --fixed to the sample--.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO.        : 6,570,170 B2  
APPLICATION NO. : 10/085968  
DATED             : May 27, 2003  
INVENTOR(S)       : Thomas M. Moore Page 1 of 1

It is certified that error appears in the above-identified patent and that said Letters Patent is hereby corrected as shown below:

In claim 2, column 6, line 42, replace "fixed to the wafer" with --fixed to the sample--.

This certificate supersedes the Certificate of Correction issued October 7, 2008.

Signed and Sealed this

Second Day of December, 2008

JON W. DUDAS  
*Director of the United States Patent and Trademark Office*